United States Patent [19]

Cleary

[11] Patent Number: 4,578,223

[45] Date of Patent: Mar. 25, 1986

[54] PROCESS FOR SEPARATING SATURATED FATTY ACIDS FROM EACH OTHER

[75] Inventor: Michael T. Cleary, Elmhurst, Ill.

[73] Assignee: UOP Inc., Des Plaines, Ill.

[21] Appl. No.: 659,104

[22] Filed: Oct. 9, 1984

[51] Int. Cl.[4] ............................ C11C 1/08; C11B 3/10
[52] U.S. Cl. .................................... 260/419; 260/420; 260/427
[58] Field of Search ............................... 260/419, 427

[56] References Cited

U.S. PATENT DOCUMENTS

| | | | |
|---|---|---|---|
| 3,895,042 | 7/1975 | Taylor | 260/428 |
| 3,954,819 | 5/1976 | Husch | 260/428 |
| 3,955,004 | 5/1976 | Strouse et al. | 260/428 |
| 4,048,205 | 9/1977 | Neuzil et al. | 260/428 |
| 4,049,688 | 9/1977 | Neuzil et al. | 260/428 |
| 4,066,677 | 1/1978 | deRosset et al. | 260/428 |
| 4,210,594 | 7/1980 | Logan et al. | 260/419 |
| 4,353,839 | 10/1982 | Cleary et al. | 260/419 |
| 4,404,145 | 9/1983 | Cleary et al. | 260/419 |
| 4,444,986 | 4/1984 | Dessau | 260/428 |
| 4,495,106 | 1/1985 | Cleary et al. | 260/428 |

FOREIGN PATENT DOCUMENTS 0071037 6/1981 Japan ................................ 260/419

OTHER PUBLICATIONS

Ory et al., "Analytical Chemistry" reprint, vol. 31, p. 1447 (1959).

Primary Examiner—Werren B. Lone
Attorney, Agent, or Firm—Thomas K. McBride; William H. Page, II; Louis A. Morris

[57] ABSTRACT

A process for separating a first saturated fatty acid from a second saturated fatty acid contained in a feed mixture comprising the acids, the chain length of the first being at least two carbon atoms greater than that of the second. The process comprises contacting the feed mixture at adsorption conditions comprising a crystalline silica having a silica to alumina mole ratio of at least 12, thereby selectively adsorbing the first saturated fatty acid. The remainder of the feed mixture is then removed from the adsorbent, and the first acid recovered from the adsorbent by desorption at desorption conditions with a desorbent liquid soluble in the feed mixture and having a polarity index of at least 3.5.

10 Claims, 1 Drawing Figure

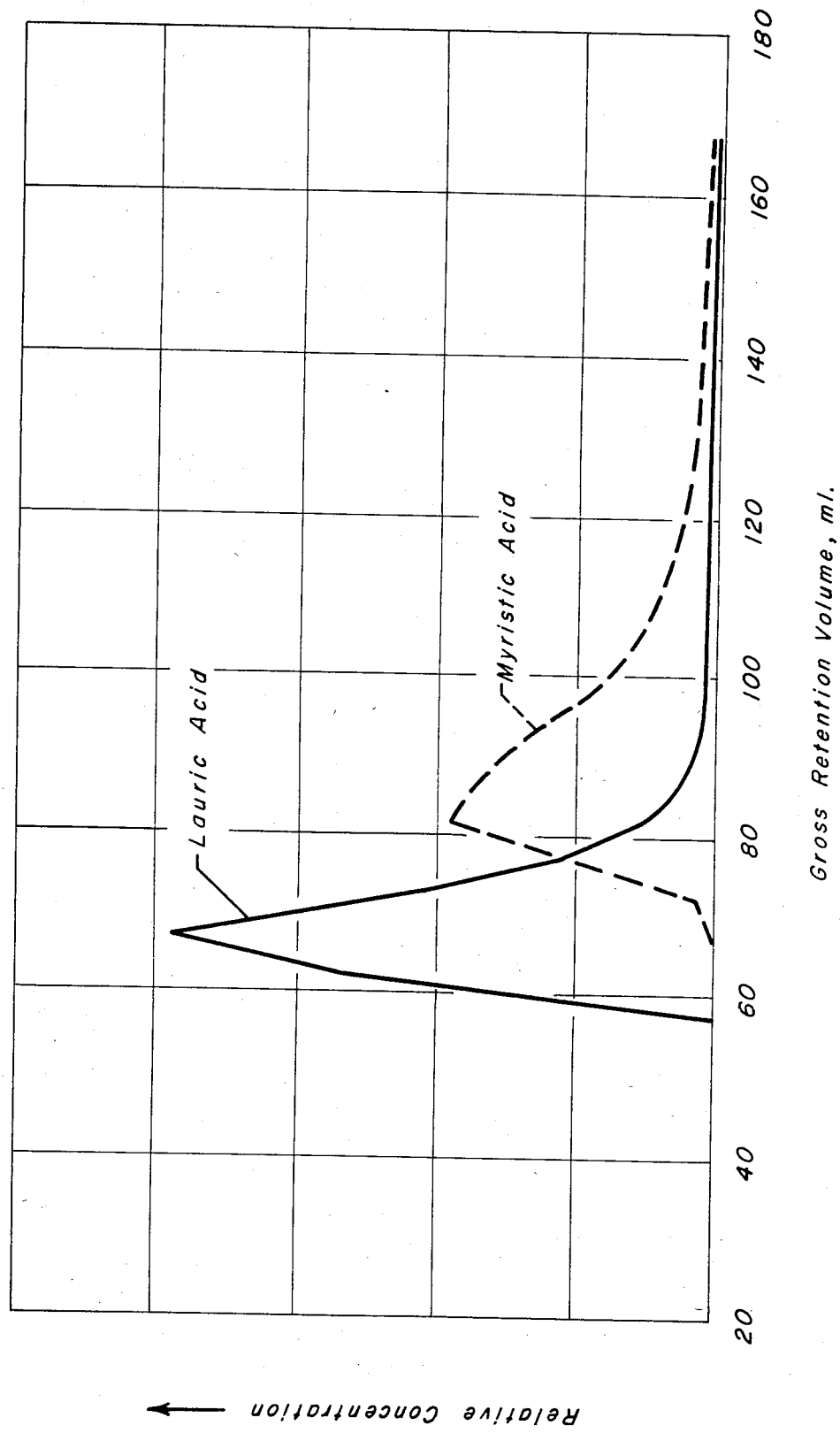

PROCESS FOR SEPARATING SATURATED FATTY ACIDS FROM EACH OTHER

BACKGROUND OF THE INVENTION

1. Field of The Invention

The field of art to which this invention pertains is the solid bed adsorptive separation of fatty acids. More specifically the invention relates to a process for separating saturated fatty acids which process employs an adsorbent comprising particular polymers which selectively adsorb one fatty acid from a feed mixture containing more than one fatty acid.

2. Background Information

It is known in the separation art that certain crystalline aluminosilicates can be used to separate certain esters of fatty acids from mixtures thereof. For example, in U.S. Pat. Nos. 4,048,205, 4,049,688 and 4,066,677, there are claimed processes for the separation of esters of fatty acids of various degrees of unsaturation from mixtures of esters of saturated and unsaturated fatty acids. These processes use adsorbents comprising an X or a Y zeolite containing a selected cation at the exchangeable cationic sites.

The use of crystalline silica for the separation of a fatty acid from a rosin acid is disclosed in U.S. Pat. No. 4,404,145 to Cleary et al. That patent also teaches the use of a displacement fluid having a minimum desired polarity index, i.e., at least 3.5. The hypothesis stated in U.S. Pat. No. 4,404,145 to Cleary et al. as to the unique suitability of its process for its claimed separation was that the silicalite pores were of a size and shape that enabled the silicalite to function as a molecular sieve, i.e., accept the molecules of fatty acids into its channels or internal structure, while rejecting the molecules of rosin acids.

The adsorptive separation of saturated fatty acids of different chain lengths from each other was disclosed in U.S. Pat. No. 4,353,839 to Cleary et al. The adsorbent used in the process of that patent was a hydrophobic insoluble crosslinked polystyrene polymer, and the desorbent a mixture of dimethylformamide and water.

U.S. Pat. No. 4,444,986 to Dessau discloses the use of a high silica zeolite for the separation of compounds of the same homologous series, including acid substituents of hydrocarbons, with the separation occurring in the presence of a solvent, including a polar solvent.

The present invention is based on the discovery that crystalline silica is highly suitable as an adsorbent for the separation process of this invention in that it exhibits relative selectivity for a long chain saturated fatty acid with respect to a shorter chain saturated fatty acid when used with an appropriate desorbent.

SUMMARY OF THE INVENTION

In brief summary my invention is, in one embodiment, a process for separating a first saturated fatty acid from a mixture comprising the first saturated fatty acid and a second saturated fatty acid, the chain length of the first being at least two carbon atoms greater than that of the second. The process comprises contacting at adsorption conditions that mixture with an adsorbent comprising a crystalline silica having a silica to alumina mole ratio of at least 12, thereby selectively adsorbing the first saturated fatty acid. The remainder of the feed mixture is removed from the adsorbent, and the first saturated fatty acid recovered from the adsorbent by desorption, at desorption conditions, with a desorbent liquid soluble in the feed mixture and having a polarity index of at least 3.5.

Other embodiments of our invention encompass details about flow schemes, feed mixtures, adsorbents, desorbent materials and operating conditions, all of which are hereinafter disclosed in the following discussion of each of the facets of the present invention.

DESCRIPTION OF THE INVENTION

At the outset the definitions of various terms used throughout the specification will be useful in making clear the operation, objects and advantages of the process.

A "feed mixture" is a mixture containing one or more extract components and one or more raffinate components to be separated by the process. The term "feed stream" indicates a stream of a feed mixture which passes to the adsorbent used in the process.

An "extract component" is a compound or type of compound that is more selectively adsorbed by the adsorbent while a "raffinate component" is a compound or type of compound that is less selectively adsorbed. In this process a first fatty acid is an extract component and a second fatty acid is a raffinate component. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream likewise can vary from essentially 100% desorbent material to essentially 100% extract components. At least a portion of the extract stream and preferably at least a portion of the raffinate stream from the separation process are passed to separation means, typically fractionators, where at least a portion of desorbent material is separated to produce an extract product and a raffinate product. The terms "extract product" and "raffinate product" mean products produced by the process containing, respectively, an extract component and a raffinate component in higher concentrations than those found in the extract stream and the raffinate stream. Although it is possible by the process of this invention to produce a high purity, first or second fatty acid product (or both) at high recoveries, it will be appreciated that an extract component is never completely adsorbed by the adsorbent, nor is a raffinate component completely non-adsorbed by the adsorbent. Therefore, varying amounts of a raffinate component can appear in the extract stream and likewise, varying amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of the first saturated fatty acid to that of the less selectively adsorbed second saturated fatty acid will be lowest in the raffinate stream, next highest in the feed mixture, and the highest in the extract stream. Likewise, the ratio of the concentration of the less selectively adsorbed second saturated fatty acid to that of the more selectively adsorbed first saturated fatty acid will be highest in the raffinate stream, next highest in the feed mixture, and the lowest in the extract stream.

The term "selective pore volume" of the adsorbent is defined as the volume of the adsorbent which selectively adsorbs an extract component from the feed mixture. The term "non-selective void volume" of the adsorbent is the volume of the adsorbent which does not selectively retain an extract component from the feed mixture. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into various operational zones for efficient operations to take place for a given quantity of adsorbent in simulated moving bed embodiments of this process.

Before considering feed mixtures which can be charged to the process of our invention, brief reference is first made to the terminology and to the general production of fatty acids. The fatty acids are a large group of aliphatic monocarboxylic acids, many of which occur as glycerides (esters of glycerol) in natural fats and oils. Although the term "fatty acids" has been restricted by some to the saturated acids of the acetic acid series, both normal and branched chain, it is now generally used, and is so used herein, to include also related unsaturated acids, certain substituted acids, and even aliphatic acids containing alicyclic substituents. The naturally occurring fatty acids with a few exceptions are higher straight chain unsubstituted acids containing an even number of carbon atoms. The unsaturated fatty acids can be divided, on the basis of the number of double bonds in the hydrocarbon chain, into monoethanoid, diethanoid, triethanoid, etc. (or monoethylenic, etc.). Thus the term "unsaturated fatty acid" is a generic term for a fatty acid having at least one double bond, and the term "polyethanoid fatty acid" means a fatty acid having more than one double bond per molecule. Fatty acids are typically prepared from glyceride fats or oils by one of several "splitting" or hydrolytic processes. In all cases the hydrolysis reaction may be summarized as the reaction of a fat or oil with water to yield fatty acids plus glycerol. In modern fatty acid plants this process is carried out by continuous high pressure, high temperature hydrolysis of the fat. Starting materials most commonly used for the production of fatty acids include coconut oil, palm oil, inedible animal fats, and the commonly used vegetable oils, soybean oil, cottonseed oil and corn oil. The composition of the fatty acids obtained from the "splitter" is dependent on the fat or oil from which they were made. As detailed data for the fatty acid composition of fats have accumulated over a wide range of material, it has become more and more apparent that natural fats tend to align themselves, by their component acids, in groups according to their biological origin. Moreover, it has become clear that the fats of the simplest and most primitive organisms are usually made up from a very complex mixture of fatty acids whereas as biological development has proceeded, the chief component acids of the fats of the higher organisms have become fewer in number. In the animal kingdom this change in type is remarkably consistent and culminates, in the fats of the higher land animals, in fats in which oleic, palmitic and stearic acids are the only major components. All fats of aquatic origin contain a wide range of combined fatty acids, mainly of the unsaturated series. On passing from fats of aquatic to those of land animals there is also a marked simplification in the composition of the mixed fatty acids; most of the unsaturated acids, except oleic acid, disappear. The final result is that in most of the higher land animals the major component acids of the fats are restricted to oleic, palmitic and stearic and moreover, that about 60–65% of the acids belong to the $C_{18}$ series, saturated or unsaturated.

Lauric ($C_{12}O$) and myristic ($C_{14}O$) acids are obtained in admixture from palm oil. These acids may be used as ingredients in perfumes. Individual acids rather than the mixture, however, may be desirable so as to tailor the properties of the perfume to exactly what is required. Thus, the separations obtained by the process of the present invention would be particularly useful in the perfume industry.

Fractionation of saturated fatty acids according to molecular weight is sometimes accomplished in fractional distillation. There is somewhat of a difference in the volatility of any two fatty acids of different chain length and in practice, the utility of fractional distillation is enhanced by the absence of odd-membered acids in the natural fats, so that 2 carbon atoms is nearly always the minimum difference in chain length of the fatty acids present in a mixture. Fractionating columns in such operation are sometimes capable of producing fatty acids of 95% purity or better from the viewpoint of chain length depending on the chain length in question. It is not possible, however, to separate certain saturated fatty acids from each other by commercial fractional distillation, particularly stearic acid from palmitic acid which have carbon atom chain lengths of 18 and 16, respectively, or lauric from myristic acid which have chain lengths of 12 and 14, respectively.

Our process is directed to separating certain mixtures of saturated fatty acids. An example of a typical feed mixture is known as U.S. pharmaceutical grade "stearic acid", which in fact is about a 50—50 mixture of stearic and palmitic acids. A mixture of lauric and myristic acids is contained in coconut oil. Feed mixtures which can be charged to our process may contain, in addition to fatty acids, a diluent material that is not adsorbed by the adsorbent and which is preferably separable from the extract and raffinate output streams by fractional distillation. When a diluent is employed, the concentration of diluent in the mixture of diluent and fatty acids may be from a few vol. % up to about 90 vol. %.

Desorbent materials used in various prior art adsorptive separation processes vary depending upon such factors as the type of operation employed. In the swing bed system in which the selectively adsorbed feed component is removed from the adsorbent by a purge stream, desorbent selection is not as critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which are generally operated continuously at substantially constant pressures and temperatures to insure liquid phase, the desorbent material must be judiciously selected to satisfy many criteria. First the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Desorbent materials should additionally be substances which are easily separable from the feed mixture that is passed into the process. Both the raffinate stream and the extract stream are removed from the adsorbent in admixture with desorbent material and without a method of separating at least a portion of the desorbent material, the purity of the extract product and the raffinate product would not be very high, nor would the desorbent material be available for reuse in the process. It is therefore contemplated that any desorbent material used in this process will preferably have a substantially different average boiling point than that of the feed mixture to allow separation of at least a portion of desorbent material from feed components in the extract and raffinate streams by simple fractional distillation, thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture. Finally, desorbent materials should also be materials which are readily available and therefore reasonable in cost. In the preferred isothermal, isobaric, liquid-phase operation of the process of this invention, it has been found, as will be discussed at length hereinbelow, displacement fluids comprising a diluent soluble in the feed mixture and having a polarity index of at least 3.5 to be effective when the conditions at which the retention and displacement is carried out is from about 20° C. to about 200° C. with pressure sufficient to maintain liquid phase. When the feedstock is tallow, the preferred conditions are about 120° C. to about 150° C. with pressure sufficient to maintain liquid phase.

The prior art has also recognized that certain characteristics of adsorbents are highly desirable, if not absolutely necessary, to the successful operation of a selective adsorption process. Such characteristics are equally important to this process. Among such characteristics are: (1) adsorptive capacity for some volume of an extract component per volume of adsorbent; (2) the selective adsorption of an extract component with respect to a raffinate component and the desorbent material; and (3) sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life. The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions. Relative selectivity is shown as Equation 1 below:

$$\text{Selectivity} = (B) = \frac{[\text{vol. percent } C/\text{vol. percent } D]_A}{[\text{vol. percent} C/\text{vol. percent } D]_U} \quad \text{Equation 1}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases. Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is greater than 1, it is preferred that such selectivity approach a value of 2. Like relative volatility, the higher the selectivity the easier the separation is to perform. Higher selectivities permit a smaller amount of adsorbent to be used. The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

The adsorbent to be used in the process of this invention comprises crystalline silica having a silica/alumina mole ratio of at least 12. One such crystalline silica is known as silicalite which has a silica/alumina mole ratio of infinity, i.e., it contains no alumina. Silicalite is a hydrophobic crystalline silica molecular sieve. Silicalite is disclosed and claimed in U.S. Pat. Nos. 4,061,724 and 4,104,294 to Grose et al., incorporated herein by reference. Due to its aluminum-free structure, silicalite does not show ion-exchange behavior, and is hydrophobic and organophilic. Low alumina crystalline silica is uniquely suitable for the separation process of this invention for the reason that it exhibits relative selectivity for the longer chain saturated fatty acids, presumably because of varying degrees of electro-chemical attraction between the crystalline silica and different saturated fatty acids. This is in contradistinction to the process of aforementioned U.S. Pat. No. 4,404,145 in which the effectiveness of crystalline silica is based on the hypothesis that its pores are of a size and shape that enable it to function as a molecular sieve, i.e., accept the molecules of saturated fatty acids (which are relatively flexible) into its channels or internal structure, while rejecting the molecules of unsaturated fatty acids (which are relatively rigid), the separation from which was the concern of that patent. A more detailed discussion of silicalite may be found in the article, "Silicalite, A New Hydrophobic Crystalline Silica Molecular Sieve"; *Nature*, Vol. 271, Feb. 9, 1978, incorporated herein by reference.

Examples of other crystalline silicas suitable for use in the present invention are those having the trademark designation "ZSM" and silica/alumina mole ratios of at least 12. The ZSM adsorbents are as described in U.S. Pat. Nos. 4,309,281 and 4,444,986 to Dessau, incorporated herein by reference. The latter Dessau patent does make certain broad statements that the ZSM type zeolite may be employed to selectively sorb higher molecular weight organic compounds in the same homologous series and that the sorption may take place in the presence of a polar solvent, (although no preference is stated, and a non-polar solvent is exemplified) but is completely silent as to how desorption is to be effected, other than by stating "by conventional desorbing techniques such as stripping." In order to have a viable process, desorption is as important a criteria, if not more important, than adsorption. The present invention addresses the complete separation scheme necessary for a viable process, including the use of very specific desorbents as will be discussed hereinbelow.

Typically, adsorbents used in separative processes contain the crystalline material dispersed in an amorphous material or inorganic matrix, particularly an amorphous material having channels and cavities therein which enable liquid access to the crystalline silica. The binder aids in forming or agglomerating the crystalline particles of the crystalline silica which otherwise would comprise a fine powder. The silica molecular sieve may thus be in the form of particles such as extrudates, aggregates, tablets, macrospheres or granules having a desired particle range, preferably from about 16 to 60 mesh (Standard U.S. Mesh). Colloidal amorphous silica is an ideal binder for crystalline silica in that like the crystalline silica itself this binder exhibits no reactivity for the free fatty acids. The preferred silica is marketed by DuPont Company under the trademark "Ludox." The crystalline silica powder is dispersed in the Ludox which is then gelled and treated so as to substantially eliminate hydroxyl groups, such as by thermal treatment in the presence of oxygen at a temperature from about 450° C. to about 1000° C. for a minimum period from about 3 hours to about 48 hours. The crystalline silica should be present ih the silica matrix in amounts ranging from about 75 wt. % to about 98 wt. % crystalline silica based on volatile free composition.

It has been observed that even crystalline silica may be ineffective in separating fatty acids from each other. It is hypothesized that hydrogen-bonded dimerization reactions occur in which there is an alignment between the molecules of the fatty acids. These dimerization reactions may be represented by the formula:

$$FA + FA \rightleftharpoons (FAFA)$$

where FA stands for fatty acids. The dimers would preclude separation of the fatty acids by blocking access to the adsorbent or reducing the selectivity. This hindrance to separation caused by the presence of dimers does not appear to be a significant problem in the aforementioned process for separation of esters of fatty acids.

It has been discovered that the above dimerization reactions may be minimized if the desorbent is properly selected. There are liquids which exhibit the property of minimizing dimerization. The measure of this property was found to be the polarity index of the liquid. Polarity index is as described in the article, "Classification of the Solvent Properties of Common Liquids"; Snyder, L. J. *Chromatography*, 92, 223 (1974), incorporated herein by reference. The minimum polarity index of the desorbent required for the process of the present invention is 3.5. Polarity indexes for certain selected diluents are as follows:

| Solvent | Polarity Index |
| --- | --- |
| Isooctane | −0.4 |
| n-Hexane | 0.0 |
| Toluene | 2.3 |
| p-Xylene | 2.4 |
| Benzene | 3.0 |
| Methylethylketone | 4.5 |
| Acetone | 5.4 |
| 3-Pentanone (estimated) | 4.4 |

The adsorbent may be employed in the form of a dense compact fixed bed which is alternatively contacted with the feed mixture and desorbent materials. In the simplest embodiment of the invention the adsorbent is employed in the form of a single static bed in which case the process is only semi-continuous. In another embodiment a set of two or more static beds may be employed in fixed bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Moving bed or simulated moving bed flow systems, however, have a much greater separation efficiency than fixed bed systems and are therefore preferred. In the moving bed or simulated moving bed processes, the retention and displacement operations are continuously taking place which allows both continuous production of an extract and a raffinate stream and the continual use of feed and displacement fluid streams. One preferred embodiment of this process utilizes what is known in the art as the simulated moving bed countercurrent flow system. The operating principles and sequence of such a flow system are described in U.S. Pat. No. 2,985,589 incorporated herein by reference. In such a system, it is the progressive movement of multiple liquid access points down a molecular sieve chamber that simulates the upward movement of molecular sieve contained in the chamber. Reference can also be made to a paper entitled "Continuous Adsorptive Processing—A New Separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheme.

Another embodiment of a simulated moving bed flow system suitable for use in the process of the present invention is the co-current high efficiency simulated moving bed process disclosed in our assignee's U.S. Pat. No. 4,402,832, incorporated by reference herein in its entirety.

The size of the units which can utilize the process of this invention can vary anywhere from those of pilot plant scale (see for example our assignee's U.S. Pat. No. 3,706,812, incorporated herein by reference) to those of commercial scale and can range in flow rates from as little as a few cc an hour up to many thousands of gallons per hour.

It is contemplated with any flow scheme used to carry out the present invention that at least a portion of the extract output stream will pass into a separation means wherein at least a portion of the desorbent can be separated to produce an extract product containing a reduced concentration of desorbent. Preferably, but not necessary to the operation of the process, at least a portion of the raffinate output stream will also be passed to a separation means wherein at least a portion of the desorbent can be separated to produce a desorbent stream which can be reused in the process and a raffinate product containing a reduced concentration of desorbent. The separation means will typically be a fractionation column, the design and operation of which is well known to the separation art.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Desorption conditions will thus include, as hereinbefore mentioned, a pressure sufficient to maintain a liquid phase. Adsorption conditions may include, as a matter of convenience, the same range of temperatures and pressures as used for desorption conditions.

A dynamic testing apparatus is employed to test various adsorbents with a particular feed mixture and desorbent material to measure the adsorbent characteristics of adsorptive capacity, selectivity and exchange rate. The apparatus consists of an adsorbent chamber comprising a helical column of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a tracer and of a particular extract component or of a raffinate component or both, all diluted in desorbent, is injected for a duration of several minutes. Desorbent flow is resumed, and the tracer and the extract component or the raffinate component (or both) are eluted as in a liquid-solid chromatographic operation. The effluent can be analyzed onstream or alternatively effluent samples can be collected periodically and later analyzed separately by analytical equipment and traces of the envelopes of corresponding component peaks developed.

From information derived from the test adsorbent, performance can be rated in terms of void volume, retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance between the peak envelopes. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width, the faster the desorption rate. The desorption rate can also be characterized by the distance between the center of the tracer peak envelope and the disappearance of an extract component which has just been desorbed. This distance is again the volume of desorbent pumped during this time interval.

The following working example is presented to illustrate the process of the present invention and is not intended to unduly restrict the scope and spirit of the claims attached hereto.

EXAMPLE

This example presents the results of using Ludox bound silicalite for separating myristic acid from about a 50—50 mixture of myristic and lauric acids diluted in desorbent in a volume ratio of desorbent to acid mixture of 10:1. The desorbent used was 100% 3-pentanone.

Data was obtained using the pulse test apparatus and procedure previously described at a temperature of 120° C. Specifically, the adsorbent was placed in a 70 cc helical coiled column and the following sequence of operations was used. Desorbent material was continuously run downflow through the column containing the adsorbent at a flow rate of 1.2 ml/min. At a convenient time, the flow of desorbent material was stopped, and a 5 cc sample of feed mixture was injected into the column via a sample loop and the flow of desorbent material was resumed. Samples of the effluent were automatically collected in an automatic sample collector and later analyzed by chromatographic analysis.

The FIGURE is a graphical presentation of the results of the pulse tests. The FIGURE shows that myristic acid is more strongly adsorbed than lauric acid, particularly for the desorbent used. Furthermore, the separation achieved for this combination was substantial and clearly of commercial feasibility.

I claim as my invention:

1. A process for separating a first saturated fatty acid from a second saturated fatty acid contained in a feed mixture comprising said acids, the chain length of said first saturated fatty acid being at least two carbon atoms greater than that of said second saturated fatty acid, said process comprising contacting said feed mixture at a temperature in the range of from about 20° to about 200° C. and a pressure sufficient to maintain liquid phase with an adsorbent comprising a crystalline silica having a silica to alumina mole ratio of at least 12, thereby selectively adsorbing said first saturated fatty acid, removing the remainder of the feed mixture from the adsorbent, and recovering said first saturated fatty acid from said adsorbent by desorption a temperature in the range of from about 20° to about 200° C. and a pressure sufficient to maintain liquid phase with a desorbent liquid selected from the group consisting of methyl ethyl ketone, acetone and 3-pentanone.

2. The process of claim 1 wherein said first saturated fatty acid comprises myristic acid, and said second saturated fatty acid comprises lauric acid.

3. The process of claim 1 wherein said process is effected with a simulated moving-bed flow system.

4. The process of claim 3 wherein said simulated moving-bed flow system is of the countercurrent type.

5. The process of claim 3 wherein said simulated moving-bed flow system is of the co-current high efficiency type.

6. The process of claim 1 wherein said adsorbent comprises silicalite.

7. The process of claim 1 wherein said adsorbent is bound with amorphous silica.

8. The process of claim 1 in which the desorbent liquid is 3-pentanone.

9. The process of claim 8 wherein said first fatty acid comprises myristic acid and said second fatty acid comprises lauric acid.

10. The process of claim 2 wherein said desorbent liquid is 3-pentanone.

* * * * *